United States Patent
Suh et al.

(10) Patent No.: US 6,602,074 B1
(45) Date of Patent: Aug. 5, 2003

(54) DENTAL COMPOSITE LIGHT CURING SYSTEM

(75) Inventors: Byoung I. Suh, Oakbrook, IL (US); Wayne Vinson, Eugene, OR (US)

(73) Assignee: Bisco, Inc., Schaumburg, IL (US)

(*) Notice: Subject to any disclaimer, the term of this patent is extended or adjusted under 35 U.S.C. 154(b) by 0 days.

(21) Appl. No.: 09/530,236

(22) PCT Filed: Oct. 23, 1998

(86) PCT No.: PCT/US98/22544
§ 371 (c)(1),
(2), (4) Date: Aug. 2, 2000

(87) PCT Pub. No.: WO99/21505
PCT Pub. Date: May 6, 1999

Related U.S. Application Data

(60) Provisional application No. 60/063,446, filed on Oct. 29, 1997.

(51) Int. Cl.[7] .................................................. A61C 5/00
(52) U.S. Cl. ........................ 433/228.1; 433/29; 433/215
(58) Field of Search .......................... 433/29, 215, 229, 433/228.1

(56) References Cited

U.S. PATENT DOCUMENTS

| | | | |
|---|---|---|---|
| 3,605,039 A | 9/1971 | Harris et al. ................ | 331/94.5 |
| 3,655,483 A | 4/1972 | Borrel et al. ................ | 156/272 |
| 3,666,645 A | 5/1972 | Ransohoff .............. | 204/159.22 |
| 3,763,442 A | 10/1973 | McMahan .............. | 331/94.5 D |
| 3,801,202 A | 4/1974 | Breaux ........................ | 356/85 |
| 3,850,675 A | 11/1974 | Miller ..................... | 117/93.31 |
| 3,931,589 A | 1/1976 | Aisenberg et al. .... | 331/94.5 PE |
| 3,943,046 A | 3/1976 | De Sorga et al. ....... | 204/159.23 |
| 3,962,656 A | 6/1976 | Peressini ............. | 331/94.5 PE |
| 3,962,657 A | 6/1976 | Redman et al. ............ | 332/7.51 |
| 3,967,214 A | 6/1976 | Thatcher .............. | 331/94.5 PE |
| 3,970,962 A | 7/1976 | Peressini et al. ...... | 331/94.5 PE |

(List continued on next page.)

FOREIGN PATENT DOCUMENTS

| | | |
|---|---|---|
| DE | 28 42 938 A1 | 4/1980 |
| DE | 37 06 852 C2 | 10/1987 |
| EP | 750889 A1 | 1/1997 |
| FR | 2 629 999 | 10/1989 |
| JP | 6292692 | 10/1994 |
| WO | WO 99/37239 A1 | 7/1999 |

OTHER PUBLICATIONS

J.R. Bausch et al., *Clinical Significance of Polymerization Shrinkage of Composite Resins*, J. Prosth. Dent., vol. 48, No. 1 (Jul. 1982), pp. 59–67.

C.L. Davidson et al., *The Competition Between the Composite–Dentin Bond Strength and the Polymerization Contraction Stress*, J. Dent. Res. vol., 63, No. 12 (Dec. 1984), pp. 1396–1399.

C.L. Davidson, *Resisting the Curing Contraction with Adhesive Composites*, J. Prosth. Dent., vol. 55, No. 4 (Apr. 1986), pp. 446–447.

(List continued on next page.)

*Primary Examiner*—Nicholas D. Lucchesi
(74) *Attorney, Agent, or Firm*—Howrey Simon Arnold & White, LLP

(57) ABSTRACT

A process for preparing dental restorations includes the steps of applying a composite restorative material onto a prepared tooth followed by the application of light to the composite of intensity sufficient to penetrate the composite to initiate polymerization. Light application is then suspended for a period of time sufficient to allow for the relaxation of internal stresses created by the initial polymerization of the composite. Light is subsequently applied to the composite to complete polymerization.

A curing light is utilized which includes variably-adjustable, multiple power and timing settings.

11 Claims, 2 Drawing Sheets

U.S. PATENT DOCUMENTS

| | | | |
|---|---|---|---|
| 4,007,430 A | 2/1977 | Fletcher et al. | 331/94.5 D |
| RE29,421 E | 9/1977 | Scott | 331/94.5 Q |
| 4,053,845 A | 10/1977 | Gould | 330/4.3 |
| 4,061,986 A | 12/1977 | Barker | 331/94.5 PE |
| 4,161,436 A | 7/1979 | Gould | 204/157.1 R |
| 4,165,265 A | 8/1979 | Nakabayashi et al. | 204/159.14 |
| 4,178,221 A | 12/1979 | Boutin et al. | 204/159.23 |
| 4,182,665 A | 1/1980 | Mibu et al. | 204/159.15 |
| 4,191,622 A | 3/1980 | Phillips et al. | 204/159.22 |
| 4,203,080 A | 5/1980 | Wright et al. | 331/94.5 D |
| 4,224,525 A | 9/1980 | Phillips et al. | 250/531 |
| 4,230,766 A | 10/1980 | Gaussens et al. | 428/288 |
| 4,298,005 A | 11/1981 | Mutzhas | 128/396 |
| 4,308,120 A | 12/1981 | Pennewiss et al. | 204/159.23 |
| 4,313,969 A | 2/1982 | Matthews et al. | 427/44 |
| 4,329,421 A | 5/1982 | Wisnosky et al. | 430/322 |
| 4,351,853 A | 9/1982 | Jochum et al. | 427/2 |
| RE31,279 E | 6/1983 | Mefferd et al. | 372/107 |
| 4,411,931 A | 10/1983 | Duong | 427/54.1 |
| 4,421,784 A | 12/1983 | Troue | 427/54.1 |
| 4,447,151 A | 5/1984 | McLellan et al. | 356/218 |
| 4,477,901 A | 10/1984 | Braband et al. | 371/15 |
| 4,479,225 A | 10/1984 | Mohler et al. | 372/97 |
| 4,504,231 A | 3/1985 | Koblitz et al. | 433/228 |
| 4,522,593 A | 6/1985 | Fischer | 433/136 |
| 4,544,467 A | 10/1985 | Bunker et al. | 204/159.24 |
| 4,551,100 A | 11/1985 | Fischer | 433/218 |
| 4,571,377 A | 2/1986 | McGinniss et al. | 430/81 |
| 4,573,159 A | 2/1986 | Aagano et al. | 372/34 |
| 4,578,055 A | 3/1986 | Fischer | 604/2 |
| 4,582,701 A | 4/1986 | Piechota, Jr. | 424/52 |
| 4,611,327 A | 9/1986 | Clark et al. | 372/58 |
| 4,613,972 A | 9/1986 | Bettman | 372/107 |
| 4,615,033 A | 9/1986 | Nakano et al. | 372/99 |
| 4,615,034 A | 9/1986 | Von Gunten et al. | 372/99 |
| 4,625,317 A | 11/1986 | Kolb et al. | 372/88 |
| 4,635,272 A | 1/1987 | Kamide et al. | 372/87 |
| 4,656,635 A | 4/1987 | Baer et al. | 372/27 |
| 4,661,070 A | 4/1987 | Friedman | 433/203.1 |
| 4,665,524 A | 5/1987 | Cotter | 372/18 |
| 4,674,092 A | 6/1987 | Cannon | 372/33 |
| 4,687,663 A | 8/1987 | Schaeffer | 424/52 |
| 4,696,010 A | 9/1987 | Eastman | 372/34 |
| 4,697,269 A | 9/1987 | Ohara | 372/34 |
| 4,698,835 A | 10/1987 | Ono et al. | 378/136 |
| 4,704,583 A | 11/1987 | Gould | 330/4.3 |
| 4,713,825 A | 12/1987 | Adsett | 372/107 |
| 4,716,569 A | 12/1987 | Bees | 372/38 |
| 4,717,605 A | 1/1988 | Urban et al. | 428/1 |
| 4,723,257 A | 2/1988 | Baer et al. | 372/108 |
| 4,727,554 A | 2/1988 | Watanabe | 372/36 |
| 4,746,685 A | 5/1988 | Masuhara et al. | 522/13 |
| 4,762,962 A | 8/1988 | Yada et al. | 522/3 |
| 4,769,824 A | 9/1988 | Seki | 372/107 |
| 4,784,135 A | 11/1988 | Blum et al. | 128/303.1 |
| 4,817,096 A | 3/1989 | Nighan et al. | 372/5 |
| 4,843,110 A | 6/1989 | Kubota et al. | 522/14 |
| 4,849,320 A | 7/1989 | Irving et al. | 430/280 |
| 4,862,469 A | 8/1989 | Couillaud et al. | 372/33 |
| 4,872,936 A | 10/1989 | Engelbrecht | 156/307.3 |
| 4,877,401 A | 10/1989 | Higuchi et al. | 433/215 |
| 4,887,271 A | 12/1989 | Taylor | 372/29 |
| 4,895,517 A | 1/1990 | Fischer | 433/224 |
| 4,896,330 A | 1/1990 | Krueger et al. | 372/65 |
| 4,904,872 A | 2/1990 | Grix et al. | 250/423 R |
| 4,923,905 A | 5/1990 | Masuhara et al. | 522/24 |
| 4,941,873 A | 7/1990 | Fischer | 604/54 |
| 4,968,251 A | 11/1990 | Darnell | 433/216 |
| 4,971,556 A | 11/1990 | Ritano | 433/102 |
| 4,983,380 A | 1/1991 | Yarborough | 424/52 |
| 4,983,381 A | 1/1991 | Torres Zaragoza | 424/53 |
| 4,989,217 A | 1/1991 | Ostler | 372/107 |
| 4,990,089 A | 2/1991 | Munro | 433/215 |
| 4,995,540 A | 2/1991 | Colin et al. | 222/132 |
| 5,002,854 A | 3/1991 | Fan et al. | 430/270 |
| 5,002,855 A | 3/1991 | Fan et al. | 430/270 |
| 5,005,181 A | 4/1991 | Yoshioka et al. | 372/59 |
| 5,007,737 A | 4/1991 | Hirleman, Jr. | 356/336 |
| 5,007,837 A | 4/1991 | Werly | 433/226 |
| 5,009,885 A | 4/1991 | Yarborough | 424/53 |
| 5,031,768 A | 7/1991 | Fischer | 206/370 |
| 5,032,178 A | 7/1991 | Cornell | 106/35 |
| 5,033,650 A | 7/1991 | Colin et al. | 222/137 |
| 5,040,182 A | 8/1991 | Spinelli et al. | 372/18 |
| 5,041,280 A | 8/1991 | Smigel | 424/52 |
| 5,043,361 A | 8/1991 | Kubota et al. | 522/10 |
| 5,055,743 A | 10/1991 | Ekstrand | 315/111.51 |
| 5,092,022 A | 3/1992 | Duret | 29/160.6 |
| 5,093,385 A | 3/1992 | Ali | 522/57 |
| 5,098,299 A | 3/1992 | Fischer | 433/215 |
| 5,098,303 A | 3/1992 | Fischer | 433/215 |
| 5,123,845 A | 6/1992 | Vassiliadis et al. | 433/215 |
| 5,127,730 A | 7/1992 | Brelje et al. | 356/318 |
| 5,137,448 A | 8/1992 | Dougherty et al. | 433/214 |
| 5,149,659 A | 9/1992 | Hakuta et al. | 436/55 |
| 5,154,861 A | 10/1992 | McBrierty et al. | 264/1.4 |
| 5,175,077 A | 12/1992 | Grossa | 430/327 |
| 5,181,214 A | 1/1993 | Berger et al. | 372/34 |
| 5,181,215 A | 1/1993 | Sam et al. | 372/34 |
| 5,214,658 A | 5/1993 | Ostler | 372/23 |
| 5,217,654 A | 6/1993 | Buckley | 264/22 |
| 5,238,744 A | 8/1993 | Williams et al. | 428/412 |
| 5,240,415 A | 8/1993 | Haynie | 433/216 |
| 5,246,371 A | 9/1993 | Fischer | 433/217 |
| 5,254,114 A | 10/1993 | Reed, Jr. et al. | 606/15 |
| 5,269,684 A | 12/1993 | Fischer | 433/90 |
| 5,275,564 A | 1/1994 | Vassiliadis et al. | 433/226 |
| 5,280,536 A | 1/1994 | Dumond et al. | 372/82 |
| 5,286,257 A | 2/1994 | Fischer | 604/82 |
| 5,289,919 A | 3/1994 | Fischer | 206/571 |
| 5,290,259 A | 3/1994 | Fischer | 604/218 |
| 5,298,532 A | 3/1994 | Ali | 522/27 |
| 5,300,331 A | 4/1994 | Schaeffer | 427/493 |
| 5,306,143 A | 4/1994 | Levy | 433/29 |
| 5,318,562 A | 6/1994 | Levy et al. | 606/16 |
| 5,318,999 A | 6/1994 | Mitra et al. | 522/57 |
| 5,321,715 A | 6/1994 | Trost | 372/69 |
| 5,324,200 A | 6/1994 | Vassiliadis et al. | 433/224 |
| 5,328,462 A | 7/1994 | Fischer | 604/82 |
| 5,332,092 A | 7/1994 | Fischer | 206/365 |
| 5,349,591 A | 9/1994 | Weston et al. | 372/25 |
| 5,356,291 A | 10/1994 | Darnell | 433/216 |
| 5,360,834 A | 11/1994 | Popall et al. | 522/36 |
| 5,364,267 A | 11/1994 | Fischer | 433/26 |
| 5,376,006 A | 12/1994 | Fischer | 433/215 |
| 5,387,103 A | 2/1995 | Fischer | 433/89 |
| 5,409,631 A | 4/1995 | Fischer | 252/186.25 |
| 5,425,641 A | 6/1995 | Fischer | 433/226 |
| 5,425,953 A | 6/1995 | Sintov et al. | 424/404 |
| 5,444,104 A | 8/1995 | Waknine | 522/24 |
| 5,445,523 A | 8/1995 | Fischer et al. | 433/90 |
| 5,449,703 A | 9/1995 | Mitra et al. | 522/57 |
| 5,464,348 A | 11/1995 | Fischer et al. | 433/26 |
| 5,467,362 A | 11/1995 | Murray | 372/5 |
| 5,472,991 A | 12/1995 | Schmitt et al. | 522/4 |
| 5,478,235 A | 12/1995 | Schuldt et al. | 433/37 |
| 5,501,579 A | 3/1996 | Kimura et al. | 417/269 |
| 5,501,599 A | 3/1996 | Rechmann | 433/215 |
| 5,521,227 A | 5/1996 | Palazzotto et al. | 522/4 |
| 5,534,559 A | 7/1996 | Leppard et al. | 522/64 |
| 5,534,562 A | 7/1996 | Jensen et al. | 523/118 |

| | | | |
|---|---|---|---|
| 5,536,758 A | 7/1996 | Boldt | 522/4 |
| 5,550,853 A | 8/1996 | Ostler | 372/34 |
| 5,558,230 A | 9/1996 | Fischer et al. | 226/570 |
| 5,575,655 A | 11/1996 | Darnell | 433/216 |
| 5,603,701 A | 2/1997 | Fischer | 604/211 |
| 5,611,687 A | 3/1997 | Wagner | 433/80 |
| 5,618,273 A | 4/1997 | Fischer | 604/211 |
| 5,632,739 A | 5/1997 | Anderson et al. | 606/2 |
| 5,635,162 A | 6/1997 | Fischer | 424/49 |
| 5,643,206 A | 7/1997 | Fischer | 604/82 |
| 5,645,428 A | 7/1997 | Yarborough | 433/215 |
| 5,665,066 A | 9/1997 | Fischer | 604/82 |
| 5,667,386 A | 9/1997 | Black et al. | 433/213 |
| 5,685,712 A | 11/1997 | Fischer | 433/26 |
| 5,692,900 A | 12/1997 | Fischer | 433/26 |
| 5,697,903 A | 12/1997 | Fischer | 604/82 |
| 5,697,918 A | 12/1997 | Fischer et al. | 604/227 |
| 5,700,148 A | 12/1997 | Fischer et al. | 433/217.1 |
| 5,708,052 A | 1/1998 | Fischer et al. | 523/116 |
| 5,722,829 A | 3/1998 | Wilcox et al. | 433/90 |
| 5,722,833 A | 3/1998 | Fischer et al. | 433/217.1 |
| 5,725,843 A | 3/1998 | Fischer | 424/49 |
| 5,746,598 A | 5/1998 | Fischer | 433/216 |
| 5,766,011 A | 6/1998 | Sibner | 433/215 |
| 5,770,105 A | 6/1998 | Fischer | 252/186.25 |
| 5,770,182 A | 6/1998 | Fischer | 424/49 |
| 5,775,904 A | 7/1998 | Riitano | 433/102 |
| 5,776,127 A | 7/1998 | Anderson et al. | 606/2 |
| 5,785,955 A | 7/1998 | Fischer | 424/49 |
| 5,800,163 A | 9/1998 | Rueggeberg et al. | 433/9 |
| 5,803,734 A | 9/1998 | Knutson | 433/136 |
| 5,816,804 A | 10/1998 | Fischer | 433/90 |
| 5,846,058 A | 12/1998 | Fischer | 433/216 |
| 5,847,020 A | 12/1998 | Ibsen et al. | 522/84 |
| 5,851,512 A | 12/1998 | Fischer | 424/49 |
| 5,855,870 A | 1/1999 | Fischer | 424/49 |
| 5,856,373 A | 1/1999 | Kaisaki et al. | 522/25 |
| 5,858,332 A | 1/1999 | Jensen et al. | 424/53 |
| 5,860,806 A | 1/1999 | Pranitis, Jr. et al. | 433/80 |
| 5,865,623 A * | 2/1999 | Suh | 433/228.1 |
| 5,868,769 A | 2/1999 | Rosenblood et al. | 606/161 |
| 5,882,201 A | 3/1999 | Salem | 443/216 |
| 5,890,900 A | 4/1999 | Fischer et al. | 433/149 |
| 5,890,901 A | 4/1999 | Fischer et al. | 433/149 |
| 5,912,470 A | 6/1999 | Eibofner et al. | 250/504 H |
| 5,922,307 A | 7/1999 | Montgomery | 424/53 |
| 5,925,715 A | 7/1999 | Mitra | 525/293 |
| 5,947,278 A | 9/1999 | Sawhney et al. | 206/216 |
| 5,967,778 A | 10/1999 | Riitano | 433/77 |
| 5,985,249 A | 11/1999 | Fischer | 424/49 |
| 6,008,264 A | 12/1999 | Ostler et al. | 522/4 |
| 6,102,696 A | 8/2000 | Osterwalder et al. | 433/29 |
| 6,103,203 A * | 8/2000 | Fischer | 422/186 |

OTHER PUBLICATIONS

A.J. Feilzer et al., *Setting Stress in Composite Resin in Relation to Configuration of the Restoration*, J Dent. Res., vol. 66, No. 11 (Nov. 1987), pp. 1636–1639.

A.J. Feilzer et al., *Increased Wall–to–Wall Curing Contraction in Thin Bonded Resin Layers*, J. Dent. Res., vol. 68, No. 1 (Jan. 1988), pp. 48–50.

C.M. Kemp–Scholte et al., *Marginal Sealing of Curing Contraction Gaps in Class V Composite Resin Restorations*, J. Dent. Res., vol. 67, No. 5 (May 1988), pp. 841–845.

C.M. Kemp–Scholte et al., *Complete Marginal Seal of Class V Resin Composite Restorations Effected by Increased Flexibility*, J. Dent. Res., vol. 69, No. 6 (Jun. 1990), pp. 1240–1243.

C.M. Kemp–Scholte et al., *Marginal Integrity Related to Bond Strength and Strain Capacity of Composite Resin Restorative Systems*, J. Prosth. Dent., vol. 64, No. 6 (Dec. 1990), pp. 698–664.

A.J. Feilzer et al., *Setting Stresses in Composites for Two Different Curing Modes*, Dent. Mater., vol. 9 (Jan. 1993), pp. 25.

T.F. Lundeen et al., *Clinical Significance of Dental Anatomy, Histology, Physiology, and Occlusion*, in: The Art and Science of Operative Dentistry (Mosby, St. Louis, 1995), pp. 10–19.

M. R. Bouschilcher et al., *Effect of Composite Type, Light Intensity, Configuration Factor and Laser Polymerization on Polymerization Contraction Forces*, Am. J. Dent., vol. 10, No. 2 (Apr. 1997), pp. 88–96.

International Search Report in International (PCT) Application No. PCT/US98/22544 dated Oct. 23, 1998.

International Preliminary Examination Report with annexes in International (PCT) Application No. PCT/US98/22544 dated Feb. 3, 2000.

Koran et al.; *Stress Reduction in Composites Due to Two–Step–Polymerization*; Journal of Dental Research, 75, Abstract #2393 (1997).

Mehl et al., *Physical Properties and Gap Formation of Light–cured Composites With and Without 'Softstart–polymerization'*, Journal of Dentistry, 25(3–4): 321–330 (May 1997).

Mehl et al., *Softstartpolymerisation von Kompositen in Klasse–V–Kavitäten*, Dtsch. Zahnärztl Z. 52: 824–827 (1997) [English translation provided.].

Mehl et al., *The Influence of Pre–curing on the Material Properties of Composite Resins*, Journal of Dental Research, 74, Abstract #496 (1995).

Reinhardt et al., *Unsicherheiten bei der Prüfung von Photopolymerisaten*, Dtsch. Zahnärztl Z. 36: 635–640 (1981) [English translation provided.].

Sakaguchi et al., *Light Intensity Effects on Degree of Cure of Posterior Composite IADR*, 1972:1–4 (1997).

Uno, et al.; *Marginal Adaptation of a Restorative Resin Polymerized at Reduced Rate*; Scand. J. Dent. Res., 99(5): 440–444 (Oct. 1991).

* cited by examiner

DENTAL COMPOSITE LIGHT CURING SYSTEM

CROSS-REFERENCE TO RELATED APPLICATIONS

This is the U.S. National phase of International Application No. PCT/US98/22544 filed Oct. 23, 1998, which claims the priority benefit under 35 U.S.C. §119(e) of U.S. provisional patent application Serial No. 60/063,446 filed Oct. 29, 1997.

BACKGROUND OF THE INVENTION

1. Field of the Invention

The invention relates to light curing apparatus and processes for preparing dental restorations.

2. Description of Related Technology

Shrinkage of light- and self-cured dental composites used for direct, intraoral restorations has long been a concern of dental investigators because of the potential for micro-leakage to occur at a tooth-restoration interface. When composite restorations cure, they shrink as a result of the polymerization of the resin monomers in the composite. The volumetric shrinkage of composites may be in the range of approximately 3–4%. Micro-leakage resulting from such shrinkage can contribute to recurrent tooth decay, staining, and sensitivity.

Investigators have demonstrated that self-cured dental composites display less shrinkage stress than light-cured composites, because self-cured composites exhibit the ability to flow to allow the relaxation of stress during a relatively slow curing period, usually several minutes. (See Davidson et al, JDR, 63:1396–1399(1984); Feilzer et al., Dent. Mater., 9:2–5 (1993)). When a composite is light-cured it quickly polymerizes to a fairly high cross-link density, for example, within just a few seconds. Such quick polymerization does not provide sufficient time for the composite to relax and relieve the stress.

Light-induced polymerization shrinkage has long been a concern in the dental industry because of its potential to cause "debonding" at the tooth-restoration interface, especially when adhesive strengths are not optimal. With an adhesive bond strength of sufficient magnitude, the polymerization shrinkage can be redirected to reduce the stress at the restoration-tooth interface. This redirected polymerization shrinkage, however, can create internal stresses in the restorative material (composite resin) or the remaining tooth structure detrimental to the long term success of the restored dentition.

The use of advanced dental adhesives may cause the fracture of the more brittle tooth enamel at the margin of the restoration in response to the polymerization shrinkage. As a result of the enamel fracture, micro-leakage can then progress to the detriment of the restored dentition. Enamel is an anisotropic brittle substance consisting mainly of rods or prisms, having a high elastic modulus and low tensile strength resulting in a very rigid structure. (See The Art and Science of Operative Dentistry, 3rd. Ed., C. M. Sturdevant, T. M. Robertson, H. O. Heymann, and J. R. Sturdevant editors, 1995, Mosby-Year Book, Inc., St. Louis Mo., pp. 12–18). Forces or stresses applied perpendicular to the direction of the enamel rods can much more easily fracture enamel as compared to parallel directed stress. The upper portion of Class I or Class II (MOD) restorations, above the dentin-enamel junction (DEJ), typically will have enamel rods parallel to the bonding line to be formed between adhesive and enamel. Because of the relatively weak nature of enamel, if stressed perpendicular to the rod direction, Class I or larger Class II restorations are susceptible to fractures within the enamel structure relatively close to the bond line forming cracks parallel to the bond line.

Of the several different classes of restorations, the Class I or Class II (e.g., MOD) type with their high amount of bonded surface area has in particular been the focus of much research due to its inherent high stress potential with good adhesives. Several studies on methods to counteract stresses in dental restorations have been conducted, including varied composite insertion methods into the dental cavity (e.g., bulk and incremental), composite shrink minimization, stress relaxation by flow to allow built-up stress to decrease, and strain measurements by numerous groups. See C. M. Kemp-Scholte and C. L. Davidson, J. Dent Res., vol. 67, p. 841, (1988); J. R. Bausch, et al., J. Prosthetic Dent., vol. 48, vol. 59 (1982); A. J. Feilzer, et al., J. Dent. Res., vol. 66, p. 1636; C. Davidson, J. Prosthetic Dent., vol. 55, p. 446 (1986); A. Feilzer, et al., J. Dent. Res., vol. 68, p. 48 (1989); C. M. Kemp-Scholte and C. L. Davidson, J. Prost. Dent, vol. 64, p. 658 (1990); C. M. Kemp-Scholte and C. L. Davidson, J. Dent. Res, vol. 69, p. 1240 (1990), C. L. Davidson, et al., J. Dent. Res., vol. 63, p. 1396 (1984); M. R. Bouschlicher, et al., Amer. J. Dent. vol. 10, pp. 88–96 (1997). It has been found that slow, self-cured composites reduce the rate of shrinkage stress formation which may cause enamel cracking.

In contrast, the visible-light curing process currently used with dental composites is a very fast, free-radical-initiated process where the bulk of the polymerization reaction typically is completed within just a few seconds. This quick process has always been considered a great advantage to the clinician but can lead to very high stress rates within the tooth structure. Such high rates of stress formation are known to cause premature failures in brittle materials (See Organic Coatings: Science and Technology, Vol. II, Z. W. Wicks, el al., John Wiley & Sons, New York, pp 105–31 (1994) and references cited therein; see also, An Introduction to the Mechanical Properties of Solid Polymers, I. M. Ward and D. W. Hadley, John Wiely & Sons, New York, Chapter 12 (1993) and references cited therein).

A study conducted by the inventors to illustrate stress formation problems with light-cured composites as compared to self-cured composites included the steps of placing an increment of a light-cure composite (ÆLITEFIL™, Bisco, Inc., Schaumburg, Ill.) into a Class I cavity of approximately 3×3×3 mm up to the dento-enamel junction. After a light cure of ten seconds at 600 milliwatts per square centimeter (hereinafter $mW/cm^2$), a second increment of the same light-cure composite was added to the cavo-surface margin and the composite was cured using a high intensity light (e.g., ten seconds at 600 $mW/cm^2$) on each of the buccal, lingual, and occlusal surfaces. An enamel crack was observed on one side of the restoration (see FIG. 4). The inventors performed an identical study using a dual-curing (self-light) dental composite (DUO-LINK, Bisco, Inc., Schaumburg, Ill.) for the second increment and allowing the self-cure process to proceed for five minutes before light curing. In this latter study, no enamel cracks were observed (See FIG. 5). No cracks were observed in dentin for either the light-cured or self-cured samples studied. (The reason why enamel cracked and dentin did not crack is most likely due to dentin's higher flexibility (lower modulus). Thus, it was determined that the slower, self-curing composite could provide excellent structural integrity compared to light-cured composites. However, self-cured composites are not clinically ideal for use as occlusal surface restorative materials. Thus, for occlusal surface restorative applications, light-cured composites remain the most desirable option. However, latest trends with light curing are towards curing dental composites even faster, using higher and higher intensity curing systems, which can only create higher stressed restorations.

Commercial curing systems usually use fixed intensities, typically at 400 to 600 mW/cm$^2$, which are not adjustable by the user. Additionally, commercial curing systems employ curing times that are usually pre-programmed at a minimum of ten seconds to a maximum of sixty seconds in ten second increments. Such curing systems require dental clinicians to use high curing intensities for durations which will result in high stress formation. Shorter than ten second duration curing times are not provided for by commercially-available curing systems.

Known devices used to cure visible-light-initiated dental composites are often called light-curing (LC) units or guns, since the hand-held portion of most units looks like a gun with a trigger for activating light. A typical visible light curing unit includes a base unit that typically sits on a counter in a dental operatory and houses the electronics that operate the light. The base unit may have a timer, some type of holder (also referred to as a cradle) for the gun, and an "off-on" switch. There is an electrical cord for plugging the base unit into a wall outlet, and an umbilical cord that attaches the base unit to the hand-held gun. Some LC units may include an on-board radiometer for periodically checking the output intensity of the light, with the readout typically being an LED. Such LC units have an aperture located on the base where a light tip (also referred to as a light guide) is placed. When the light tip is positioned accordingly in the aperture and the light is activated, a reading is registered, usually in mW/cm$^2$ intensity units.

A typical visible light curing unit also includes a gun that houses the light bulb, cooling fan, finger trigger, and a port for the light guide. The cooling fan operates to dissipate heat generated by the light bulb, and operates for a variable amount of time after the light bulb has been turned off. Turning off the base unit prematurely before the cooling cycle is complete can possibly cause damage to the visible light curing unit. Light bulbs are manually accessed and replaced by disassembling part of the gun. The finger trigger when depressed activates the light bulb for a pre-programed time. Depressing the finger trigger a second time will interrupt the cooling cycle and deactivate the light bulb. Typical wavelength of visible light used in commercial typical light curing units is about 400–500 nanometers (nm).

The light tip or guide tip is a cylindrical extension residing in the port at the front end of the gun and exists to deliver the exiting light to the patient. Tips usually have a slight curve at its distal end for easy access and positioning into the oral cavity, and are commonly available in several different diameters. the most common being 2 millimeters (mm), 3 mm, 8 mm, 11 mm, and 13 mm. A removable amber-colored eye-protection-shield is usually slidably attached to the tip. This shield can be adjusted to the right or left side of the tip to provide the operators viewing protection. Tips may be detached for cleaning sterilizing.

An exemplary cordless visible light-curing unit is commercially-available under the name PROLITE from Dentsply/Caulk, Milford, Del. This unit includes a cordless gun, meaning the base does have an electrical cord, but the gun is not tethered to the base unit like most curing units. The base has three indicator lights: POWER, CHARGING, and READY. The amber-colored CHARGING light is activated (i.e. on) any time the unit has been used and is being re-charged. Once charged, the amber light is deactivated (i.e. turns off) and the green light is activated. There is no "off" switch on the base unit. The gun sits in a cradle that doubles as a charger and base unit. An on-board radiometer gives: (1) a green light if the power exceeds 300 mW/mm$^2$, (2) an amber light if the power is 150–300 mW/mm$^2$; (3) and a red light if the power is below 150 mW/mm$^2$. A timer is located on the back of the gun handle and is displayed in a small LED window. Curing times can be set in ten second increments from 10–60 seconds. When the light is activated, the timer counts down to zero from the present amount of time. By setting the timer to zero, the gun can be used in a continuous curing mode. In the continuous curing mode, the timer counts up continuously to 120 seconds before automatically deactivating the light. As noted above, the curing unit is cordless, and, therefore, a battery is installed in the gun handle. It is recommended to completely discharge the battery once per month and then recharge the battery. A completely charged gun will cure for 14 full minutes prior to running out of power. Four consecutive beeps alert the user when the battery is about to run out of power. A 35 Watt light bulb is used having a life of 30 hours.

Another commercially-available cordless visible light curing unit is sold under the name VIVALUX II by Ivoclar-Vivadent, Amherst, N.Y. This cordless light-curing unit has two charging docks or receptacles. A typical three-light system warns the user of the charging status, wherein a green indicates that the unit is charged, a yellow light indicates that the unit is currently charging, and a red light indicates the unit requires service. The base unit has no "on-off" switch. The gun for this unit has no on-board radiometer. The gun has a digital display on the top rear of the gun handle, which displays an icon that looks like a battery when the gun is fully charged. When the gun is discharged, the battery icon appears almost empty and blinks. This unit has no timer, there is one beep after 20 seconds, two beeps after 40 seconds, and three beeps after 60 seconds. Maximum curing time without recharging is 8.5 to 9 minutes. This unit has a 35 Watt light bulb having a life of 1000 hours.

An exemplary commercially-available light-curing unit that has a cord is OPTILUX 500, which is made and sold by Demetron/Kerr, Danbury, Conn. The base unit for this corded, light curing unit has a built-in radiometer for checking power output of the light. The radiometer is read via an LED numerical readout. A soft-touch control pad is located on a face of the base unit. The pad can be used to program various time cycle settings for light exposure. The settings include 10, 20, 30, 40, 50, 60 seconds cycles or continuous curing. A first switch on the back of the base enables the operator to set a beeping signal to sound every 10 or 20 seconds as well as beeping at the end of a preset cycle. A second switch enables the operator to control the volume of the beeping signal, and a third switch is used for resetting the total elapsed hours of the current bulb when the light bulb is replaced. A finger switch on the gun activates and deactivates the light bulb. A preset timing is used to automatically deactivate the light bulb source at the completion of that preset time period. An 80 Watt halogen bulb is used in the gun. The base unit can be wall-mounted if so desired.

Another commercially-available, corded, light-curing unit is available under the name OPTILUX 401/403, from Demetron/Kerr, Danbury, Conn. The base unit of this light-curing unit has a circular know-shaped timer positioned on a top surface which allows time cycle presetting of 10, 20, 30, 40, 50 and 60 second exposures. A beeping signal signifies the end of a preset time period. An 80 Watt bulb is used in the gun, the bulb having a life of about 80 hours.

Another commercially-available, corded light-curing unit is sold under the name SPECTRUM by Dentsply/Caulk. Milford, Del. The base unit of this light-curing unit consists of a built-in radiometer and a removable cradle that can be mounted or placed in a convenient location. Optionally, the base unit can be wall mounted. Instead of an LED readout for the radiometer, the base unit uses three lights to indicate the status of curing power, wherein: (a) a green light signifies acceptable power, (b) a yellow light signifies caution, (c) and a red light indicates that replacement or service is needed. A short sounding beep signifies the beginning of the curing cycle and a long beep indicates the end of the cycle. Available time cycle settings include: 10, 20 or 60 seconds. The gun uses a 49 Watt light bulb having a life of 20 hours.

Another commercially-available, corded light-curing unit is sold under the name XL3000 by 3M, St. Paul, Minn. The base unit of this light-curing unit can be wall-mounted or placed on a counter top. A swing out door houses a spare bulb for convenience. The gun was a 75 Watt lightbulb having life of 40 hours. An on-board radiometer causes illumination of a green light if the power output is acceptable; if power is unacceptable, no illumination occurs. A single beep indicates both the beginning and end of a cure cycle. A double-beep occurs if the cure cycle has been manually interrupted. A timer is located on the back handle of the gun, having time cycle settings of 10, 20, 30 40 seconds or XT (for extended curing for a maximum of 200 seconds). A beep sounds every ten second during an XT time cycle setting.

Another commercially-available, corded light-curing unit is sold under the name ELIPAR HIGHLIGHT by ESPE, Norristown, Pa. This unit features a standard setting with full power (700 mW/cm$^2$) and a second time cycle setting with a "2-Step" mode. In the 2-Step mode, the light intensity is at low power (150 mW/cm$^2$) during the first 10 seconds and then immediately switches to full power (700 mW/cm$^2$) for the remaining 30 or 50 seconds of curing depending on user requirements. An advertisement for the unit appearing in DPR Europe, November 1996, states that the initial low power is used "to minimize the risk of fracture and optimize marginal adhesion, thus maximizing the life of the final restoration. The initial low light intensity of 150 mW/cm$^2$ reportedly extends the plastic (low viscosity) phase of the material, allowing material stresses to balance out." ESPE product literature states that "[i]n the 2-Step Mode, the lighting intensity is reduced during the first 10 seconds to reduce stress during initial and final curing of the material." There are four curing time cycle settings available in the standard mode: 20, 40 and 60 seconds and "2-Step" mode. The 2-step mode is allowed to function only if 40 second or 60 second time cycles are chosen. This unit features several custom-programmable beeping functions. For example, the unit can sound a beep when the light is activated or turned off, beeping can occur at 10 seconds, then two beeps at 20 seconds and 60 seconds. A radiometer built-in to the base unit activates a green light to indicate adequate power, and a white light to indicate inadequate power. Since this unit has a 2-step mode for different curing powers, a microprocessor monitors the voltage supply. This guarantees constant light power throughout the entire life of the bulb. The bulb is 75 Watts, no life-expectancy is listed. It is noted that the ELIPAR HIGHLIGHT product literature does not state that the rate of stress formation is reduced; it states only that stress is reduced. There is no clear evidence the ELIPAR HIGHLIGHT light-curing unit reduces stress. Also, according to such a system, an operator cannot adjust or change the time cycle setting to cure at low intensity when using the 2-step mode. Also this light-curing unit provides no opportunity to pause between low and high intensity curing.

Another commercially-available corded, light-curing unit is sold under the name COLOTOLUX 4 by Coltene/Whaledent, Mahwah, N.J. The base unit has a ring-like cradle for the gun. A green LED on-off switch is located on the base. A timer, using a large dial, is located on the base and allows selection of 10, 20, 30, 40, 50 and 60 second curing intervals. The built-in radiometer has an LED readout. When the gun is activated, a beep sounds at the beginning of the curing cycle. The gun uses a 75 Watt light bulb having a life of 28 hours.

Listed below by manufacturer are additional commercially-available, corded intra-oral light curing systems

| Manufacturer | Name of Light System |
| --- | --- |
| Lares Research, Chico, CA | APOLLO S |
| Coltene/Whaledent, Mahwah, NJ | COLTOLUX 3 |
| Degussa, South Plainfield, NJ | DEGULUX |
| Pro-Den, Portland, OR | EXECUTOR |
| Pro-Den, Portland, OR | POLY-LITE 1000 |
| Dolan-Jenner, Lawrence, MA | FIBER-LITE |
| Ivoclar-Vivadent, Amherst, NY | HELIOLUX DLX |
| Den-Mat, Santa Maria, CA | MARATHON TWO |
| Megadenta, Rudeberg, Germany | MEGULUX CS |
| Demetron/Kerr, Danbury, CT | OPTILUX 150 |
| Demetron/Kerr, Danbury, CT | OPTILUX 360 |
| Demetron/Kerr, Danbury, CT | VCL 300 |
| Heraeus Kulzer, Irvine, CA | TRANSLUX CL |
| 3M, St. Paul, MN | XL1500 |
| Henry Shein, Port Wash., NY | MAXIMIA 250 |
| Henry Shein, Port Wash., NY | ECONOMY Curing Light |

Listed below by manufacturer are additional commercially-available, cordless intra-oral curing systems.

| Manufacturer | Name of Light System |
| --- | --- |
| Litema Dental, Baden, Germany | ARCUS 1 |
| Litema Dental, Baden, Germany | ARCUS 2 |

SUMMARY OF THE INVENTION

It is an object of the invention to overcome one or more of the problems described above.

It also is an object of the invention to put the concept or stress-relaxation known from self-cure composites into practice in the art of light-cure dental restoration. This is only feasible if a far less than complete (e.g., partial) curing has occurred prior to allowing the relaxation to occur, and if the relaxing times required for the process are short enough to be reasonable for a dental clinician. Described herein is a composite curing process acceptable to the standard dental clinician and a visible-light curing unit design which will allow for the generation of lower rates of initial stress formation in Class I or larger Class II dental restorations, resulting in far reduced enamel fractures and more sound restorations.

A process according to the invention includes the steps of applying a composite restorative material onto a prepared tooth followed by the application of visible light (having a wavelength of approximately 400 to 500 nanometers) to the composite of intensity and time sufficient to penetrate the composite to initiate polymerization. Light application is then suspended for a period of time sufficient to allow for the relaxation of internal stresses created by the initial polymerization of the composite. Light, usually of a higher intensity, is subsequently applied to the composite to complete polymerization.

Also according to the invention, a curing light is utilized which includes multiple power and timing settings.

Other objects and advantages of the invention will be apparent to those skilled in the art from the following detailed description taken in conjunction with the drawings and the appended claims.

BRIEF DESCRIPTION OF THE DRAWINGS

For a more complete understanding of the process and apparatus of the invention reference should be made to the following detailed description and drawing figures wherein.

Figure 1:
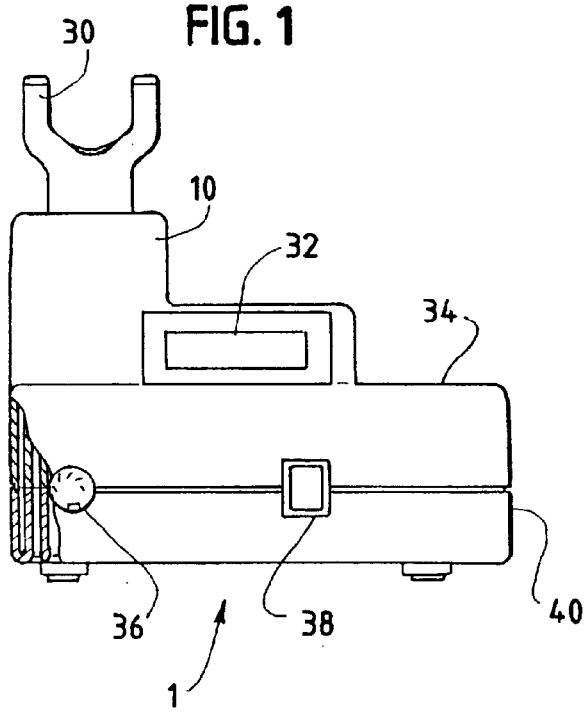
FIG. 1 is a front view of a base unit of a light curing device for use according to the invention, with portions removed to show the detail thereof.

While the present invention is susceptible of embodiment in various forms, there is illustrated in the drawing figures and will hereafter be described a specific embodiment of the present invention, with the understanding that the present description is intended as illustrative, and is not intended to limit the invention to the specific embodiment described and illustrated herein.

DETAILED DESCRIPTION OF PREFERRED EMBODIMENTS

According to the invention, the speed of a polymerization reaction of a dental composite is reduced to provide lower stress rate formation, thereby reducing or eliminating shrinkage stress. The reaction rate of light-induced polymerization can be moderated by several means (See Radiation Curing Science and Technology, S. Peter Pappas, editor, Plenum Press, New York (1992)). One such means includes decreased curing light intensity.

Too little emphasis has been placed on the importance of light cure exposure in the dental industry. In other applications using light curing to induce chemical reactions or polymerization, such as photography, UV cure coatings, and UV cure resins, exposure control is a chief concern. Light exposure is calculated as the product of light intensity ($mW/cm^2$) and time (seconds) and has units of millijoules per square centimeter ($mJ/cm^2$). For example, curing for ten seconds at 400 $mW/cm^2$ results in an exposure of 4,000 $mJ/cm^2$ or 4 $Joules/cm^2$. Thus, a twenty second cure at 200 $mW/cm^2$ is equivalent to a ten second cure at 400 $mW/cm^2$, identical exposures of 4 $Joules/cm^2$. The inventors have discovered that curing by either means results in identical cure depths, hardness, and physical strength as shown in TABLE I below:

TABLE 1

Barcol Hardness Data
Varying Intensities at Equal Exposures

| Composite | Time (sec) | Intensity ($mW/cm^2$) | Exposure ($J/cm^2$) | Barcol Hardness (n = 3) Top (SD) | Bottom (SD) |
|---|---|---|---|---|---|
| ÆLITEFIL A2[1] | 5 | 600 | 3.00 | 99.7 (0.6) | 90.3 (0.6) |
|  | 10 | 300 | 3.00 | 100.0 (0.0) | 91.7 (1.2) |
|  | 15 | 200 | 3.00 | 99.0 (0.0) | 91.3 (0.6) |
| ÆLITEFIL A3.5[1] | 5 | 600 | 3.00 | 99.0 (0.0) | 62.0 (0.6) |
|  | 10 | 300 | 3.00 | 99.0 (0.0) | 60.7 (2.6) |
|  | 15 | 200 | 3.00 | 98.0 (0.0) | 59.3 (1.5) |

[1]Bisco, Inc., Schaumburg, IL

A major difference between curing at a lower intensity and curing at a higher intensity is that the lower intensity reaction proceeds more slowly. Despite the increased time required to complete the cure, a slower cure rate is highly preferable for dental restorations at the enamel interface in order to reduce the rate of stress formation and, thereby, reduce the likelihood of damage to brittle materials, such as enamel.

The rate of stress formation in a composite being cured is related to the reaction rate of the polymerization. According to the invention, the reaction rate (and thus the stress formation rate) can be controlled by adjusting the intensity of the curing light source. Lower light intensity gives slower reaction rates and, thus, slower stress formation rates.

According to the invention, if a composite is light-cured at a low intensity for a short period to initiate polymerization, and then allowed time for the composite to relax (or re-orient), shrinkage stress can be reduced. Accordingly, a method of achieving high quality Class I or Class II restorations has been developed by carefully controlling the initial light induced polymerization reaction and by allowing time for the initially stressed composite to relax before proceeding with the cure.

Accordingly to a preferred process of the invention, light of sufficient intensity (preferably ranging between 100 $mW/cm^2$ and 300 $mW/cm^2$) must penetrate the composite resin and initiate the polymerization of the resin system. Such penetration and polymerization initiation is preferably performed for a short (pulse) initial duration. The short cure time hardens the composite sufficiently to allow a dental clinician to begin normal finishing procedures The time may vary depending on the surface hardness desired by the dental clinician for initial finishing. During the time period following the initial resin polymerization, the composite is provided time to relax the internal stresses created by the initial reactions. During said time, the resin system may creep or flow slightly as it relaxes.

Subsequent to a relaxation period of about three to about five minutes, the restoration is light cured, preferably for ten seconds at a normal light intensity of about 400 to 600 mW/cm², from each of the facial, lingual and occlusal directions to complete polymerization of the composite restoration and produce optimum physical properties. The foregoing procedure reduces bond failures and fracture of the enamel substrate. In this fashion, optimal marginal integrity can be accomplished. However, a composite resin material and light source with some degree of compatibility must be employed to be successful.

A particularly preferred, light-cure composite stress-relaxation technique according to the invention includes the step of placing an adhesive agent as described in the manufacturer's instructions. A first increment of composite restorative material is placed, as needed, to approximately the dento-enamel junction. The increment is light cured for 10 seconds at 600 mW/cm². In the case of a deep cavity, several increments and cures may be needed to reach the dento-enamel junction. For such first increment or increments of composite, a high intensity may be preferred since the distance from the composite surface to the curing tip may be several millimeters and, therefore, the resulting intensity at the surface may be lower. For example, a distance of five millimeters results in about a 25% loss of intensity, and a ten millimeter distance results in about a 50% loss of intensity.

A second increment of restorative composite is placed to the cavo-surface margin, sculpted as desired, and light cured for about 2–6 seconds at about 100–300 mW/cm² for a total exposure of about 0.6 joules/cm² from the occlusal direction, and preferably for about 3 seconds at 200 mW/cm².

Begin initial finishing and occlusal adjustment. If the composite surface feels too soft for finishing the second increment may be light cured once more at the same intensity. (Do not use a higher intensity).

After about three to five minutes have elapsed, the restoration is light cured at 400 mW/cm² or 600 mW/cm² for ten seconds each from the buccal, lingual and occlusal directions (the occlusal direction is preferably last). It is believed that most commercial composites will cure adequately at an intensity of 400 mW/cm².

After complete final finishing and polishing have been completed, the composite is re-etched and a finishing material, such as, FORTIFY™ finishing material (Bisco, Inc., Schaumburg, Ill.), is applied and light cured to complete the restoration.

The above-technique may be used on the following commercial composites: Z-100 (3M, St. Paul, Minn.), TETRIC (Ivoclar-Vivadent, Amherst, N.Y.), PRISMA TPH (Dentsply/Caulk, Milford, Del.), CHARISMA (Heraeus Kulzer, Irvine, Calif.), PRODIGY (Demetron/Kerr, Danbury, Conn.) and ÆLITEFIL (Bisco, Inc., Schaumburg, Ill.). Barcol hardness data for these composites are provided in Table II. With the exception of composites sold under the CHARISMA and PRODIGY tradenames, a 400 mW/cm² intensity final curing is recommended.

TABLE II

Barcol Hardness Data[1]
Commercial Composites

| Composite (A2) | Cure Time (sec) | Cure Intensity (mW/cm²) | Exposure (J/cm²) | Barcol Hardness (n = 3) Top | Bottom |
|---|---|---|---|---|---|
| Z-100(3M) | 10 | 400 | 4 | 101 | 101 |
|  | 10 | 600 | 6 | 102 | 101 |
| PRODIGY | 10 | 400 | 4 | 99 | 92 |
| (Kerr) | 10 | 600 | 6 | 100 | 97 |
| PRISMA TPH | 10 | 400 | 4 | 99 | 98 |
| (Caulk) | 10 | 600 | 6 | 100 | 99 |
| CHARISMA | 10 | 400 | 4 | 97 | 88 |
| (Kulzer) | 10 | 600 | 6 | 97 | 95 |
| TETRIC | 10 | 400 | 4 | 101 | 98 |
| (Vivadent) | 10 | 600 | 6 | 102 | 102 |
| ÆLITEFIL | 10 | 400 | 4 | 100 | 91 |
| (Bisco) | 10 | 600 | 6 | 101 | 98 |

[1]Samples were 2 mm thick and cured from the top side only.

A curing light for use according to the invention has been developed to allow a greater degree of versatility and options for curing procedures. The curing light includes multiple power and timing choices which can match any technique or circumstance. Through extensive research, the inventors have determined that these options, particular to the preferred curing light disclosed herein, are a great advantage to a dental practitioner. A curing light according to the invention allows the practitioner to choose several light intensities (e.g., 100, 200, 300, 400, 500, and 600 mW/cm²) and short and long curing times (e.g., 2, 3, 4, 5, 10, 20, 30, and 40 seconds, and continuous (e.g., up to 255 seconds)). Also, it allows for an easy calibration of the unit to ensure that the lower light intensities are accurate. As the light bulb ages the maximum light intensity may decrease. With a system according to the invention, the light calibration may be accomplished at any intensity. Thus, the practitioner is assured that the unit will have accurate low (100–200 mW/cm²) and medium (300–400 mW/cm²) intensity output; only the high output intensity (500–600 mW/cm²) should decrease.

Figure 2:
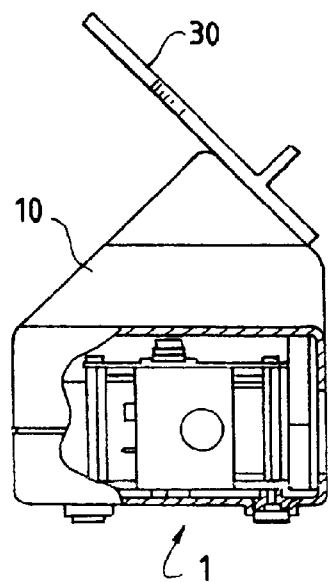
FIG. 2 is a side view of the base unit of FIG. 1, with portions removed to show the detail thereof.
Figure 3:
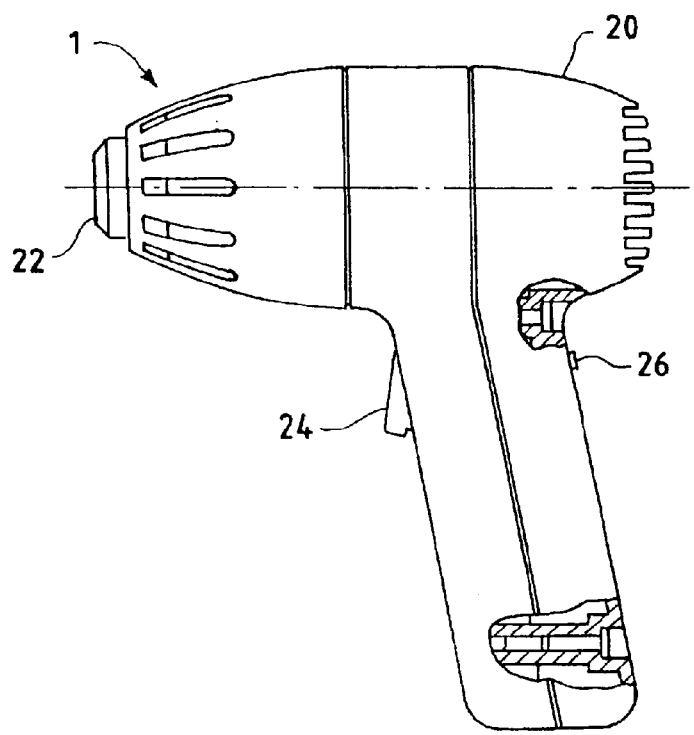
FIG. 3 is a front view of a curing light according to the invention for use with the base unit of FIG. 1, with portions removed to show the detail thereof.

With reference to FIGS. 1 to 3 wherein like reference numbers represent the same or similar elements in the various figures, a preferred light curing unit according to the invention, generally designated 1, includes a base unit 10 and a hand-held curing gun 20 having a lamp 22, a trigger switch 24, and a time/intensity selector switch 26. The base unit 10 includes a hand-piece cradle 30, a display 32, a light sensor 34, a hand-piece connector 36, and power (time/intensity) level switch 38, and a power on/off switch 40.

A preferred curing lamp 22 for use according to the invention is a 12 volt, 75 Watt halogen projection lamp (produced by Ushio, Tokyo, Japan). This is a typical type of lamp used in general visible curing lights. An internal filter system limits the wavelength of light to approximately 400–500 nm.

A preferred curing light for use according to the invention is a self-calibrating precision light source, capable of supplying light at selectable intensity levels. The selector switch 26 allows the practitioner to select curing times of 2, 3, 4, 5, 10, 20, 30, and 40 seconds, and continuous, and intensities of 100, 200, 300, 400, 500, and 600 mW/cm². The switch 38 allows the practitioner to select high power (500–600 mW/cm²), medium power (300–400 mW/cm²), or low power (100–200 mW/cm²). Self-calibration mode establishes precise adjustment of the power output and takes just a few seconds. An audible tone indicates when curing and calibration operations begin and end. Calibration can be performed as often as desired, and should be performed before each procedure to assure consistency of results.

Operation of a Preferred Curing Light

1 Power Level

For convenience, selectr controls may be accessed from either the base unit or the gun. Having verified that the correct electrical model has been connected to the wall outlet, the power level switch 38 can be set to any desired position. With a high power setting the curing lamp will continuously deliver 600 mW/cm$^2$ to the curing lamp tip for the selected duration. This setting appears in the LED display 32 as the letter "H" as the left-most digit. With a medium power setting, the curing lamp will continuously deliver 400 mW/cm$^2$ to the curing lamp tip for the selected duration. This setting appears in the LED display 32 as the letter "n" as the left-most digit. With a low power setting, the curing lamp will continuously deliver 200 mW/cm$^2$ to the curing lamp tip for the selected duration. This setting appears in the LED display 32 as the letter "L" as the left-most digit. Factory pre-sets may also be used and may be re-programmed to any desired preset the dental clinician desires.

2. Timing

The switch 26 on the back of the handpiece allows the practitioner to select possible curing times: 2, 3, 4, 5, 10, 20, 30, or 40 seconds, and continuous. Each time the switch 26 is pressed, it advances to the next time setting as shown on the display. When the longest time (40 seconds) is reached, pressing the switch 26 again will repeat the sequence beginning at 2 seconds.

3. Calibration (Verification)

The intensity may be calibrated using the on-board radiometer. To verify the power level, center the fiber optic light tip squarely within the sensor window 34. The light tip must be flat against the surface of the window or calibration results may be erratic. Press the handpiece trigger switch 24. The curing lamp will light and the word "CAL" will momentarily appear in the LED display 32. If during calibration the fiber optic tip is not placed squarely against the sensor window, the word "CAL" will begin to flash. If this occurs, press the trigger switch 24 to turn off the lamp and try again.

When the calibration is successful, the calibrated intensity level will appear in the display 32. Intensity may be calibrated at any selected intensity. If the selected intensity cannot be achieved, then the actual maximum value attainable will be displayed as a flashing value. This indicates that the unit is still operable, only at a lower actual intensity. Possible causes for such a reading would be a faulty bulb, dirty or damaged probe, dirty or damaged filters or poor optical contact with the sensor window. If the lamp is not able to produce the required power level at the fiber optic tip, then the word "FAIL" will appear on the LED display. A fan may be used to cool the optical assembly in the gun and may continue to run for approximately one minute after the light is deactivated.

When the calibration is finished, press the trigger switch 24 once to return to normal operation. If calibration fails, the procedure can be repeated. If calibration repeatedly fails, the halogen bulb should be replaced.

4. Basic Operation

Curing operation is initiated by pressing the trigger switch 24 on the handpiece 20. When this is done, the LED display 32 will show the curing time remaining and count down each second during operation.

5. Bulb Replacement

A bulb is replaced by unscrewing the front nose of the curing lamp handpiece 20. The bulb plugs into a socket be careful not to touch the bulb with bare fingers. Always use cotton gloves, clean paper towels, or an optic wipe to insert the bulb so as not to get fingerprints on the bulb or reflector. Fingerprints will degrade performance of the lamp or worse, may cause the bulb to shatter.

As discussed above, a light source utilized according to the invention must have variable timing and exposure capabilities to adequately control the exposure time, and light penetration and hence the resin polymerization. Furthermore, the composite resin initiation system (initiators) should be "tuned" or balanced to provide sufficient initial polymerization, however, not to the extent that it prevents relaxation. The initiators must also provide for optimal strength of the final restoration. This technique according to the invention has been supported by scanning electron microscopy (SEM) of the marginal integrity of the tooth/restorative interface, made on samples prepared according to the Example set forth below.

The inventive process and apparatus provide the ability to control the cure timing cycle and light intensity from both of or either of the base unit and gun. The advantage for the dental practitioner is the ability to control more easily the settings at the gun without having to reach over or around a patient or attendant to reach controls of the base unit. A preferred embodiment of the invention would include separate switches for each of the time settings and for the intensity settings, however, a single switch controlling both variables also could be used.

A preferred embodiment of the apparatus also provides the ability to dual cure with delay using different combinations of time and intensity. For example, one combination could be a time of 3 seconds at 200 mW/cm$^2$ for the initial cure, and another combination could be a time of 30 seconds at 600 mW/cm$^2$ for the final cure. The embodiment also provides the practitioner the ability to vary time and intensities as he or she desires. Furthermore, such desired time and intensities may be saved as presets using software and non-volatile memory elements disposed within the base unit. The non-volatile memory enables presets to be recalled even if power to the unit is removed, such as when transporting the device or when turning the unit off at the end of a day.

EXAMPLE

Dental Preparations for Control and Experiments According to the Invention

Class I dental preparations were created in extracted human third molars. Dimensions of the preparation were approximately 3 mm wide, 4 mm in length and 3 mm in depth. All margins were in sound supported enamel with rounded line angles and a rounded pulpal floor. All preparations were created with a high speed dental air rotor and a 1157 carbide fissure bur. All preparations were etched with 32% phosphoric acid for fifteen seconds and rinsed with copious amounts of water. The excess water was removed from the preparation with compressed air but the teeth were not desiccated. A wetting agent (AQUA-PREP™ Bisco, Inc., Schaumburg Ill.) was then applied to the surface to re-wet and promote adhesive penetration. Two applications of light-curable adhesive (ONE-STEP® adhesive manufactured by Bisco, Inc., Schaumburg, Ill.) were applied to the enamel and dentin, dispersed and dried with compressed air, and visible-light-cured for 10 seconds at 600 mW/cm$^2$ intensity using a curing light (Bisco, Inc. Schaumburg Ill.).

An additional two applications of the same type of adhesive were applied, dispersed and dried, and light-cured in the same manner as above. The remaining adhesive resin on the brush tip was then applied to the enamel and dentin surface. (Other bonding agents such as All Bond 2™ (Bisco, Inc., Schaumburg, Ill.) can be used with equivalent success. These prepared teeth were then restored as follows:

Control (Standard High-Speed/High-Intensity Cure)

An initial increment of a composite resin (ÆLITEFIL™ Vita A2® composite resin, Bisco, Inc., Schaumburg, Ill.) was placed in the preparation to the level of the dento-enamel margin and was light-cured for 10 seconds at 600 mW/cm².

Figure 4:
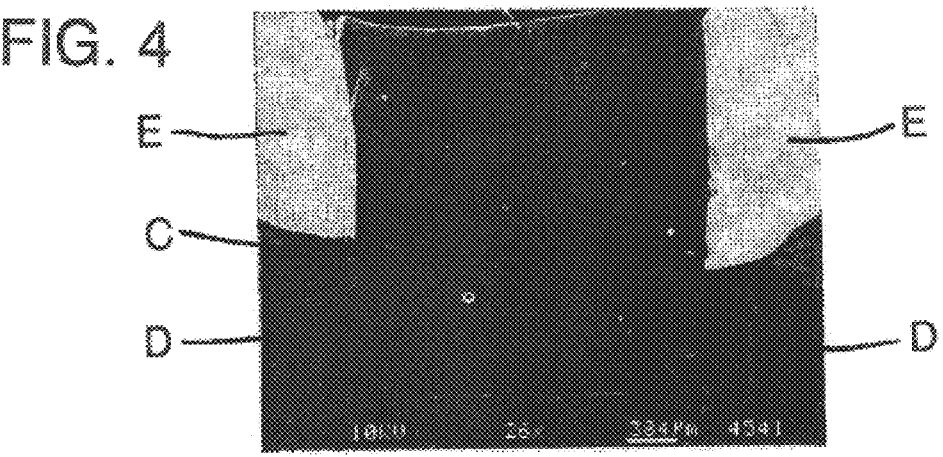
FIG. 4 is a scanning electron micrograph (hereinafter an SEM photograph) showing a restoration prepared by a conventional light-cure process (shown at 26x). "C" identifies composite; "E" identifies enamel; and "D" identifies dentin.
Figure 5:
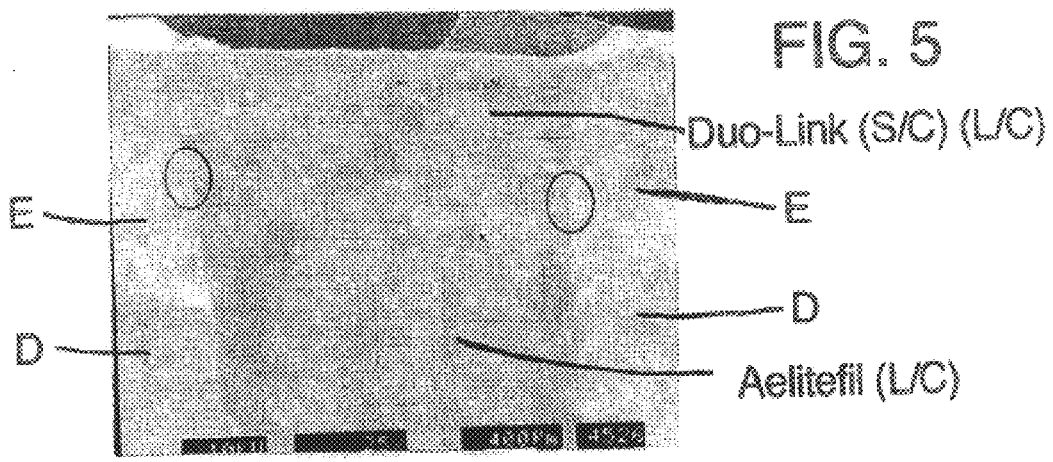
FIG. 5 is an SEM photograph showing a restoration prepared with a self/light cure composite (shown at 25x). "E" identifies enamel; "D" identifies dentin; "Aelitefil (L/C)" identifies a light-cure composite; "Duo-Link (S/C) (L/C)" identifies a self-cure/light cure composite.

A second increment of the composite resin was then placed in the preparation with intimate contact to the initial increment and the enamel cavo-surface margin and light-cured on the buccal, lingual, and occlusal surfaces, each for 10 seconds at 600 mW/cm². A sample was sectioned and examined with a scanning electron microscope (SEM) and is shown in FIG. 4.

Experiment 1 (Low Intensity Curing with 5 Minute Delay)

An initial increment of a composite resin (ÆLITEFIL™ Vita A2® composite resin, Bisco, Inc., Schaumburg, Ill.) was placed in the preparation to the level of the dento-enamel margin and was light-cured for 10 seconds at 600 mW/cm².

A second increment of the composite resin was then placed in the preparation with intimate contact to the initial increment and the enamel cavo-surface margin and light-cured for 3 seconds at 200 mW/cm².

Figure 6:
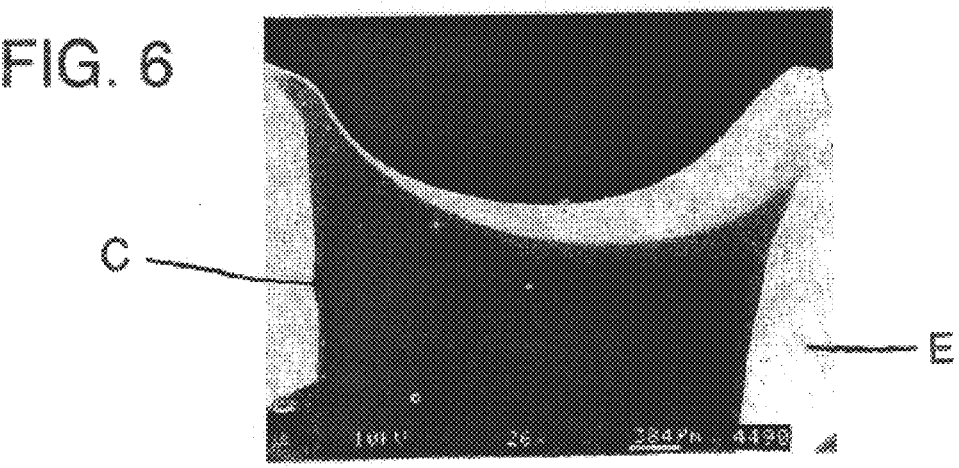
FIG. 6 is an SEM photograph showing a restoration prepared according to the invention (five minute delay) (shown at 26x). "C" identifies composite and "E" identifies enamel.

After a 5 minute delay, the buccal, lingual, and occlusal surfaces were each cured for 10 seconds at 600 mW/cm². A sample was sectioned and examined with a scanning electron microscope (SEM) and is shown in FIG. 6.

Experiment 2 (Low Intensity Curing with 3 Minute Delay)

An initial increment of a composite resin (ÆLITEFIL™ Vita A2® composite resin, Bisco, Inc., Schaumburg, Ill.) was placed in the preparation to the level of the dento-enamel margin and was light-cured for 10 seconds at 600 mW/cm².

A second increment of the composite resin was then placed in the preparation with intimate contact to the initial increment and the enamel cavo-surface margin and light-cured for 3 seconds at 200 mW/cm².

After a 3 minute delay, the buccal, lingual, and occlusal surfaces were each cured for 10 seconds at 600 mW/cm².

Test Results

Control (FIG. 4)

In all cases observed, bonding to dentin showed no defects at or near the bond line. Bonding to enamel showed no defects at the bond line but cracks in the enamel were observed parallel to the bond line at a typical distance of approximately 2–10 microns distance from the bond line. These cracks were attributed to enamel cohesive failure.

Experiment 1—Five Minute Delay (FIG. 6)

Bonding to dentin and to enamel was found to be good. No enamel cracks as observed in the Control sample described above were observed by SEM analysis.

Similar results are obtained using larger Class II type restorations (e.g., MOD type), especially in regards to cusp integrity.

Experiment 2—Three Minute Delay

Bonding to dentin and to enamel similar to samples made with a five minute delay. No enamel cracks were observed.

Similar results are obtained using larger Class II type restorations (e.g., MOD type), especially in regards to cusp integrity.

The invention provides a number of advantages. For example, curing lights and methods according to the present invention: (a) provide short, pre-programmed time selection options which are less than ten seconds (i.e., 2, 3, 4, 5 sec); (b) provide lower light intensity options for minimizing stress during curing; (c) provide typical high light intensities for final curing; and (d) provide accurate low intensities using internal calibration process. Additionally, low stress rate processes according to the invention of the application provide Class I or Class II dental restorations with good enamel structural integrity. Another excellent application of the lower stress rate processes according to the invention is with larger Class II dental restorations which are sometimes subject to stress related cusp failure during or after curing. Furthermore low stress rate processes according to the present invention: (a) are easy to use and do not greatly affect dental clinician procedures; and (b) allow use of dental composites that shrink and compensate for stresses formed.

The processes according to the present invention are applicable for all sizes of restorations but are probably best indicated to be used with more problematic and potentially higher stress Class I or Class II types. The basic (general) processes according to the present invention can be used with any typical light-curable dental composite.

The foregoing detailed description is given for clearness of understanding only, and no unnecessary limitations should be understood therefrom, as modifications within the scope of the invention will be apparent to those skilled in the art.

What is claimed is:

1. A process for curing a dental composite, comprising:
    (a) applying a composite restorative material onto a prepared tooth;
    (b) applying light to the composite of an intensity sufficient to penetrate the composite to initiate polymerization thereof;
    (b) applying light to the composite of an intensity sufficient to penetrate the composite to initiate polymerization thereof;
    (c) suspending light application for a period of time of at least 10 seconds, sufficient to allow for the relaxation of internal stresses created by the initial polymerization of the composite; and
    (d) applying light to the composite at a second intensity to complete polymerization.

2. The process of claim 1, wherein step (b) is performed using a maximum exposure of about 1 joule/cm² or less.

3. The process of claim 2, wherein step (b) is performed using an exposure of about 0.6 joule/cm² or less.

4. The process of claim 1, wherein step (c) is about three to five minutes in length.

5. The process of claim 1, wherein step (d) is performed at an intensity of about 600 mW/cm².

6. The process of claim 1, wherein step (b) comprises:
    (i) placing at least a first increment of composite restorative material onto a dento-enamel junction;
    (ii) applying light of about 600 mW/cm² for about ten seconds;
    (iii) applying a final increment of the composite restorative material to a cavo-surface margin;
    (iv) sculpting the composite;
    (v) applying light of about 200 mW/cm² for about three seconds from an occlusal direction; and
    (vi) beginning initial finishing and occlusal adjustment.

7. The process of claim 6, wherein step (c) is about three to about five minutes in length.

8. The process of claim 1, wherein the application of light in step (d) is lastly performed in the occlusal direction.

9. The process of claim 1, wherein in step (b) the intensity of light is between about 200 mW/cm² and 300 mW/cm² for about two seconds to about three seconds.

10. The process of claim 1, wherein step (d) the second intensity is between about 400 mW/cm² and 600 mW/cm² for about ten seconds each, from each of a facial, lingual and occlusal direction.

11. A process for curing a dental composite, comprising:

placing at least a first increment of composite restorative material onto a dento-enamel junction;

applying light of about 600 mW/cm² for about ten seconds;

applying a second increment of the composite restorative material to a cavo-surface margin;

applying light of about 200 mW/cm² for about three seconds;

suspending light application for a period of time of at least 10 seconds, sufficient to allow for the relaxation of internal stresses created by the initial polymerization of the composite; and applying light to the composite at an intensity between about 400 mW/cm² and about 600 mW/cm² for a period of time sufficient to complete polymerization.

* * * * *